United States Patent
Sarangapani et al.

(10) Patent No.: US 11,790,582 B2
(45) Date of Patent: Oct. 17, 2023

(54) SYSTEMS AND METHODS FOR PROVIDING VISION SIMULATION FOR PSEUDOPHAKIC PATIENTS

(71) Applicant: Alcon Inc., Fribourg (CH)

(72) Inventors: Ramesh Sarangapani, Coppell, TX (US); Lu Yin, Keller, TX (US)

(73) Assignee: Alcon Inc., Fribourg (CH)

( * ) Notice: Subject to any disclaimer, the term of this patent is extended or adjusted under 35 U.S.C. 154(b) by 259 days.

(21) Appl. No.: 17/077,941

(22) Filed: Oct. 22, 2020

(65) Prior Publication Data

US 2021/0134035 A1 May 6, 2021

Related U.S. Application Data

(60) Provisional application No. 62/928,614, filed on Oct. 31, 2019.

(51) Int. Cl.
*G06T 11/60* (2006.01)

(52) U.S. Cl.
CPC .......... *G06T 11/60* (2013.01); *G06T 2210/41* (2013.01)

(58) Field of Classification Search
CPC ...... G06T 11/60; G06T 2210/41; G16H 50/50
See application file for complete search history.

(56) References Cited

U.S. PATENT DOCUMENTS

| | | | |
|---|---|---|---|
| 2009/0187242 A1* | 7/2009 | Weeber | G02B 27/0075 623/6.24 |
| 2015/0221125 A1* | 8/2015 | Shimizu | A61B 3/1015 382/128 |
| 2017/0052393 A1 | 2/2017 | Kweon | |
| 2018/0074344 A1* | 3/2018 | Kobayashi | A61B 3/0025 |
| 2019/0189049 A1* | 6/2019 | An | G09G 3/2003 |
| 2019/0223716 A1* | 7/2019 | Abou Shousha | A61B 3/113 |
| 2020/0134882 A1* | 4/2020 | Sato | G06T 5/009 |

FOREIGN PATENT DOCUMENTS

| | | |
|---|---|---|
| EP | 0734683 A2 | 10/1996 |
| WO | 9614793 A1 | 5/1996 |

* cited by examiner

*Primary Examiner* — Said Broome
*Assistant Examiner* — Andrew Shin

(57) ABSTRACT

Systems and methods are presented for providing a vision simulation of a patient who has an eye condition. A composite image representing a real-world scene is obtained. The composite image includes multiple image layers, where each image layer represents objects that are at a particular viewing distance in the real-world scene. A first eye model representing the eye optics of the patient is generated. A second eye model representing the eye optics of a viewer is generated. The second eye model is modified by performing a mathematical function. A simulated image representing the vision of the patient is generated by convolving the first eye model and the modified second eye model with the composite image. In some embodiments, a tone mapping algorithm may also be applied to the simulated image to simulate a nighttime scene.

13 Claims, 9 Drawing Sheets

SYSTEMS AND METHODS FOR PROVIDING VISION SIMULATION FOR PSEUDOPHAKIC PATIENTS

BACKGROUND

Field of the Disclosure

The present disclosure relates to vision simulation, and more specifically, to simulating a vision of a patient implanted with an intraocular lens according to various embodiments of the disclosure.

Description of Related Art

A cataract is a condition under which a cloudy area is formed on the lens of the eye of a patient, which obstruct the vision of the patient. Cataracts are very common for people of old age. In general, cataracts can be cured by replacing the natural lens (with cataract) of the eye with an intraocular lens (IOL). Since a patient may have a pre-existing eye condition (e.g., presbyopic, etc.), the patient who have an artificial lens implanted within the eye following a cataract surgery can regain the ability to see fine spatial details at various distances (e.g., long, near, and intermediate distances, etc.) by using an IOL having an appropriate power and characteristics (e.g., multifocal IOLs) for the patient.

To illustrate the performance of various IOLs to be implanted in a patient, it is useful to present a simulated vision of the patient who will undergone a cataract surgery such that a user (e.g., the patient, other people that provide care for the patient) can decide which IOL to use when they undergo the cataract surgery. However, generating a vision simulation of a patient can be challenging, as the simulated image, which simulates what the patient perceives of a real-world scene, is presented on a flat screen (e.g., a tablet display, etc.), which is then intended to pass through the eyes of a user before being registered by the user. Therefore, there is a need in the art for providing a vision simulator that accurately simulates a vision of a pseudophakic patient.

SUMMARY

According to some embodiments, a system includes a non-transitory memory and one or more hardware processors configured to read instructions from the non-transitory memory to cause the system to perform operations comprising: accessing a first eye model representing an eye of a patient and a second eye model representing an eye of a user different from the patient; obtaining a composite image comprising a plurality of image layers corresponding to a scene, wherein each image layer in the plurality of image layers comprises an object associated with a real-world dimension and a real-world viewing distance in the scene; modifying the second eye model by performing a mathematical function to the second eye model; and generating a simulated image by applying the first eye model and the modified second eye model to each image layer in the plurality of image layers of the composite image.

According to some embodiments, a method includes generating, by one or more hardware processors, a first eye model based on biometric information of an eye of a patient; accessing, by the one or more hardware processors, a second eye model representing an eye of a user different from the patient; obtaining, by the one or more hardware processors, a composite image comprising a plurality of image layers corresponding to a scene, wherein each image layer in the plurality of image layers comprises an object associated with a real-world dimension and a real-world viewing distance in the scene; modifying, by the one or more hardware processors, the first eye model based on the second eye model; and generating, by the one or more hardware processors, a simulated image by applying the first eye model to each image layer in the plurality of image layers of the composite image.

According to some embodiments, a non-transitory machine-readable having stored thereon machine-readable instructions executable to cause a machine to perform operations including: accessing a first eye model representing an eye of a patient and a second eye model representing an eye of a user different from the patient; obtaining a composite image comprising a plurality of image layers corresponding to a scene, wherein each image layer in the plurality of image layers comprises an object associated with a real-world dimension and a real-world viewing distance in the scene; modifying the second eye model by performing a mathematical function to the second eye model; and generating a simulated image by applying the first eye model and the modified second eye model to each image layer in the plurality of image layers of the composite image.

BRIEF DESCRIPTION OF THE DRAWINGS

For a more complete understanding of the present technology, its features, and its advantages, reference is made to the following description, taken in conjunction with the accompanying drawings.

Figure 1:
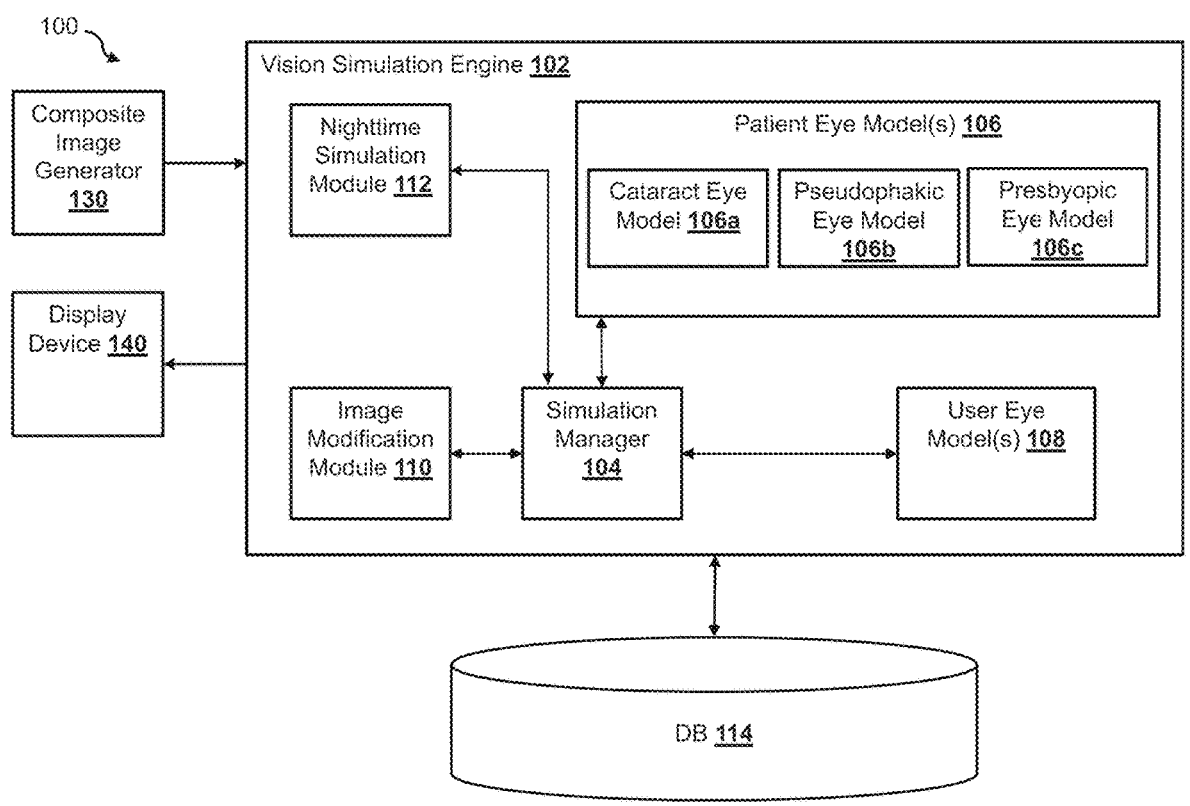
FIG. 1 is a diagram of a system for generating a simulated image according to some embodiments.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

The technology described below involves systems and methods to provide vision simulation of a patient who has an eye condition, such as a cataract condition, a presbyopic condition, or a patient who is implanted with an intraocular lens (IOL) (also referred to as a pseudophakic patient). In some embodiments, a vision simulation system is configured to present an image that simulates how the patient would perceive a real-world scene following a cataract procedure, in which their opaque natural lens is replaced by an IOL. For example, the vision simulation system may present the simulated image on a digital device (e.g., a tablet display) for viewing by one or more users.

To generate a simulated image that simulates a vision of the patient, the vision simulation system may first prepare a composite image having multiple layers of objects at different viewing distances. The composite image may be generated by combining multiple image layers of a real-world scene, where the different image layers represent objects at different viewing distances. Thus, by combining the image layers, the composite image may represent a three-dimensional real-world scene. In some embodiments, the composite image is calibrated according to how the real-world scene would be viewed by the eye of the patient. That is, all objects in the composite image are set to visual angles defined by their presumed physical sizes and viewing distances.

The vision simulation system may then establish (e.g., obtain or generate) an eye model (e.g., a first eye model) representing the eye of the patient. In some embodiments, the first eye model may include one or more point-spread functions (PSFs). In such an embodiment, the PSF represents how light from objects at different viewing distances are focused by the eye of the patient based on the properties of the eye optics of the patient in forming retinal images. The vision simulation system may then modify (e.g., blur) each layer in the composite image by convolving the first eye model with the corresponding layer, and blend all the blurred layers together to form a simulated image. The simulated image represents the realization of the real-world scene on the retina of the eye of the patient, through the eye optics. In some embodiments, the vision simulation system may use alpha-blending to merge the blurred layers into one plane, to handle object occlusion within the real-world scene. Applying the first eye model to the image of the real-world scene may generate a vision that is perceived by the eye patient. However, as discussed above, since the simulated image is presented on a flat display before a user's eye, the eye optics of the user need to be accounted for when generating the simulated image to avoid the double-pass effect.

The double-pass effect may arise in the viewer's eye (e.g., the user's eye), when the simulated image shown on the display is seen by the viewer. The double-pass effect referred herein describes the phenomenon that the simulated image, which was generated by applying the first eye model associated with the eye patient to a real-world scene, when viewed by the viewer, is further processed by the eye optics of the viewer's eye before being registered by the viewer. As such, the simulated image is perceived as being further processed (e.g., blurred) by the eye optics of the viewer (e.g., the user) when the image is registered by the viewer. In order for the viewer to perceive what the patient actually perceives when viewing the real-world scene (e.g., to eliminate the double-pass effect), the effect of the eye optics of the viewer needs to be subtracted from the simulated image before presenting the simulated image on the display.

As such, in some embodiments, the vision simulation system may establish another eye model (e.g., a second eye model) that represents the eye optics of the viewer's eye (e.g., the user's eye). The vision simulation system may then modify the second eye model by performing a mathematical function to the second eye model (e.g., performing an inverse function to the second eye model). The vision simulation system may then counter (e.g., eliminate) the double-pass effect by further applying the modified second eye model to the simulated image. For example, when modifying the composite image, the vision simulation system may modify (e.g., blur) each layer in the composite image by convolving the first eye model and the modified second eye model with the corresponding layer, and then blend the blurred layers together to form the simulated image.

The vision simulation system may then transmit and/or present the simulated image on a display device (e.g., a tablet display). It is noted that since the composite image was calibrated based on the viewing distance of the objects, such that each pixel in the composite image subtends a specific visual angle, it is required that the simulated image be viewed by the user at a preset magnification and at a distance (e.g., 40 cm) corresponding to the calibration of the composite image. Thus the vision simulation system may also instruct the user to view the simulated image at a particular viewing distance associated with the image when the simulated image is presented to the user.

The techniques described above is effective in simulating a patient's vision of a daytime scene. For a nighttime scene, the vision simulation system needs to take into account additional factors, such as the potential higher dynamic range of the nighttime scene, a human's perception of light intensity (e.g., lightness) in the dark, and the impact of light source intensity (e.g., potentially causing visual disturbance such as halo, starburst, etc.). As such, to simulate a patient's vision of a nighttime scene, the composite image obtained for the nighttime scene needs to have high dynamic range (HDR), so that the pixel intensity is linear to the physical intensities of the light sources. The vision simulation engine may first use the techniques described herein related to simulating a daytime scene to process the HDR composite image (e.g., by convolving the first eye model and the modified second eye model with the HDR composite image). The vision simulation system may further process the simulated image by applying a tone mapping algorithm to the composite image to compress the intensity range in the HDR image to a standard (or low) dynamic range such that the visibility of spatial features in the HDR image is preserved and that the image can be properly presented on a display device, which only has a standard (or low) dynamic range of display capability. In some embodiments, the vision simulation system may first segment the image into portions corresponding to light sources and portions corresponding to non-light sources, and apply the tone mapping algorithm only to the light source portion of the simulated image.

FIG. 1 illustrates a system 100 within which a vision simulation system as discussed herein may be implemented according to some embodiments. System 100 includes a composite image generator 130 for generating a composite image (e.g., regular composite image for a daytime scene or an HDR composite image for a nighttime scene, etc.), a vision simulation engine 102 for modifying the composite image based on one or more eye models to generate a simulated image, and a display device 140 for presenting the simulated image to a user. As shown, the vision simulation engine 102 includes a simulation manager 104, one or more patient eye models 106, one or more user eye models 108, an image blending module 110, and a nighttime simulation module 112. In some embodiments, the simulation manager 104 may obtain biometric information about a patient's eye (e.g., a pupil diameter, an anterior chamber depth, a corneal power, etc.) by retrieving it from a diagnostic device (not shown) or from the database 114. The simulation manager may then select, from multiple intraocular lenses (IOLs), a particular IOL for the simulated image. For example, a lens manufacturer may produce different IOLs having different optical design and/or different powers. In some embodiments, the simulation manager 104 may select, from the multiple IOLs produced by the lens manufacturer, the particular IOL based on the biometric information of the patient. For example, the simulation manager 104 may use one or more machine learning model to predict an optimal lens type for the patient to achieve a target vision quality based on the biometric information of the patient. In some embodiments, the simulation manager 104 may also present a list of the multiple IOLs on the display device 140 to enable the user (or a physician) to select the particular IOL for generating the simulated image. The simulation manager may then generate the first eye model (e.g., the patient's eye model) based on the biometric information and the selected IOL.

The simulation manager 104 may also generate a second eye model (e.g., the user eye model). In some embodiments, the simulation manager 104 may obtain biometric information of an eye of the user who will be viewing the simulated image (e.g., through a diagnostic device, etc.). Instead of measuring biometric information of the user, the simulation manager 104 of some embodiments may simply generate a generic eye model based on an eye of an average person that can be used for viewing by any user, to avoid having to measure the biometric information for different users. The simulation manager 104 may then use the image modification module 110 and/or the nighttime simulation module 112 to modify the composite image based on the first and second eye models to generate a simulated image, and may then present the simulated image on the display device 140.

Figure 2A:
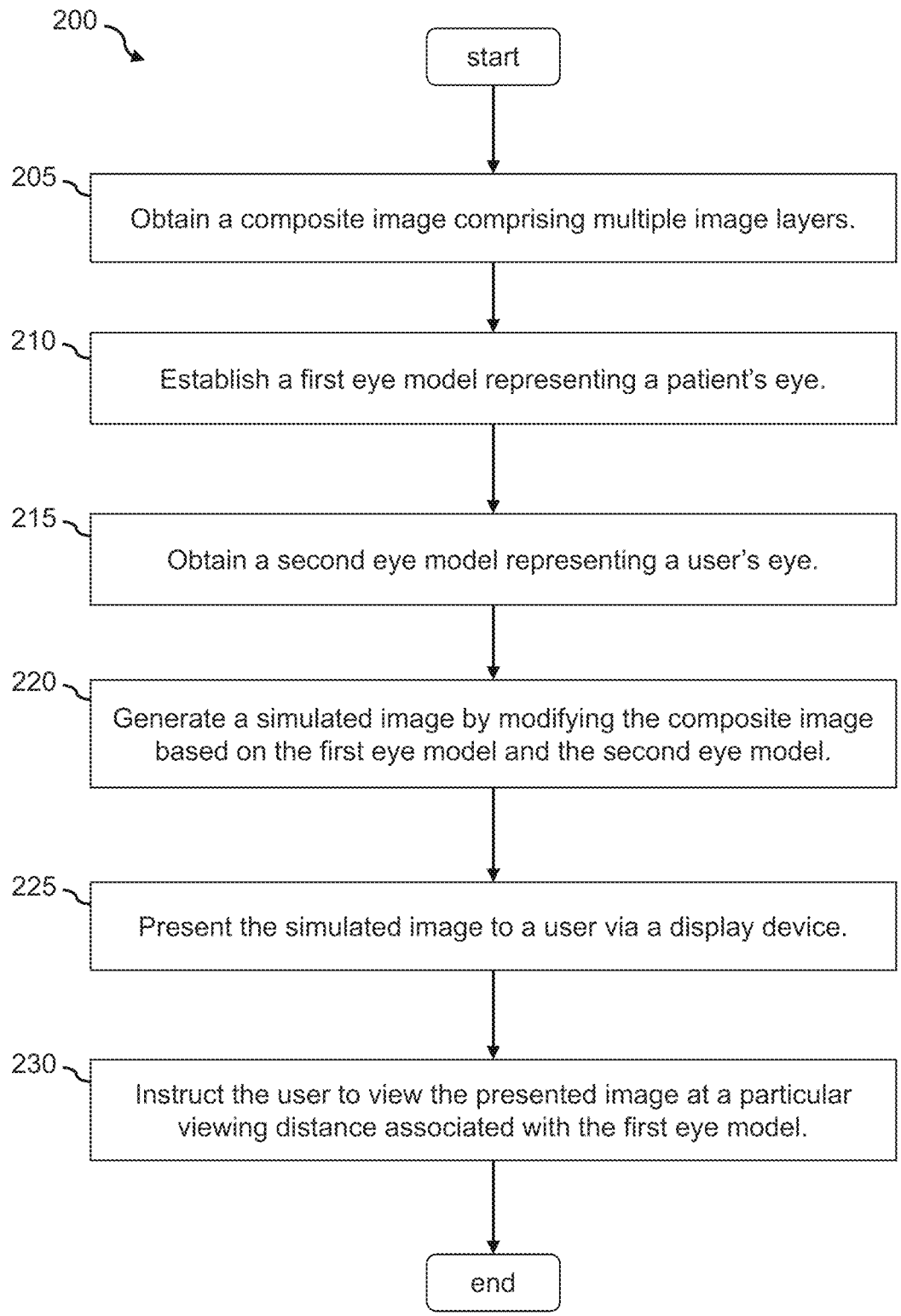
FIG. 2A illustrates a process of generating a simulated image representing a daytime scene according to some embodiments.

FIG. 2A illustrates a process 200 for providing a simulated image of a daytime scene for a user according to one embodiment of the disclosure. The simulated image represents the daytime scene perceived by a patient (e.g., through the eye optics of the patient). In some embodiments, the process 200 may be performed by the vision simulation engine 102. As discussed above, the patient may have different eye conditions, such as a cataract condition, a presbyopic condition, a pseudophakic eye condition (e.g., a patient who has undergone a cataract surgery which replaces the natural lens of the eye with an IOL). In some embodiments, the process 200 generates a simulated image that simulates how the patient would perceive a real-world scene following a cataract procedure, in which their opaque natural lens is replaced by an IOL.

Figure 3:
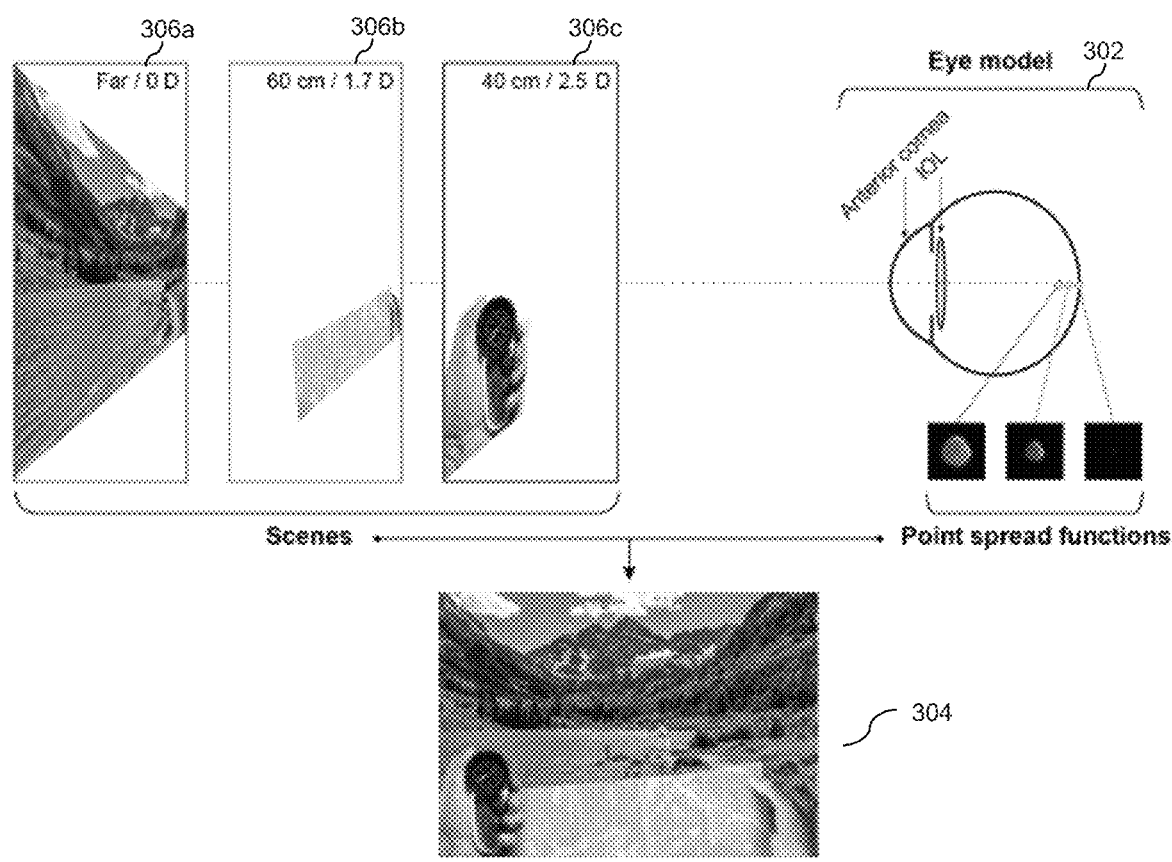
FIG. 3 illustrates a composite image according to some embodiments.

The process 200 begins by obtaining (at step 205) a composite image comprising multiple image layers. For example, the simulation manager 104 may obtain the composite image from the composite image generator 130. The composite image may be generated by combining multiple image layers of a real-world scene, where each image layer represents objects at a different viewing distance. FIG. 3 illustrates a composite image 304 that is generated by combining different image layers 306a-306c. In some embodiments, the different image layers 306a-306c represent different objects that are at different viewing distance from a real-world scene. For example, among the different image layers 306a-306c, the image layer 306a represents objects (e.g., mountains, background) that are at a far viewing distance, the image layer 306b represents objects (e.g., the map) that is at an intermediate viewing distance, and the image layer 306c represents objects (e.g., the compass) that is at a near viewing distance. Thus, by combining the image layers 306a-306c, the composite image 304 represents a three-dimensional real-world scene. In some embodiments, the composite image is calibrated according to how the real-world scene would be viewed by the eye of the eye patient. That is, all objects in the composite image are set to visual angles defined by their presumed physical sizes and viewing distances. To calibrate, each object (the objects in each layer) assumes a real-world physical size (e.g., $height_{objectPhysical}$), and a pre-defined viewing distance ($l_{viewingDistance}$). The visual angle subtended by the object can be calculated using the following equation:

$$\Theta_{object} = \operatorname{atan}\left(\frac{height_{objectPhysical}}{l_{viewingDistance}}\right) \qquad (1)$$

All layers of the composite image (e.g., the composite image 306) is scaled to have the same radian per pixel, using the following equation:

$$\Theta_{pixel} = \frac{\Theta_{object}}{height_{objectPixel}} \qquad (2)$$

Where $height_{objectPixel}$ is the height of the object in pixels.

Figure 5A:
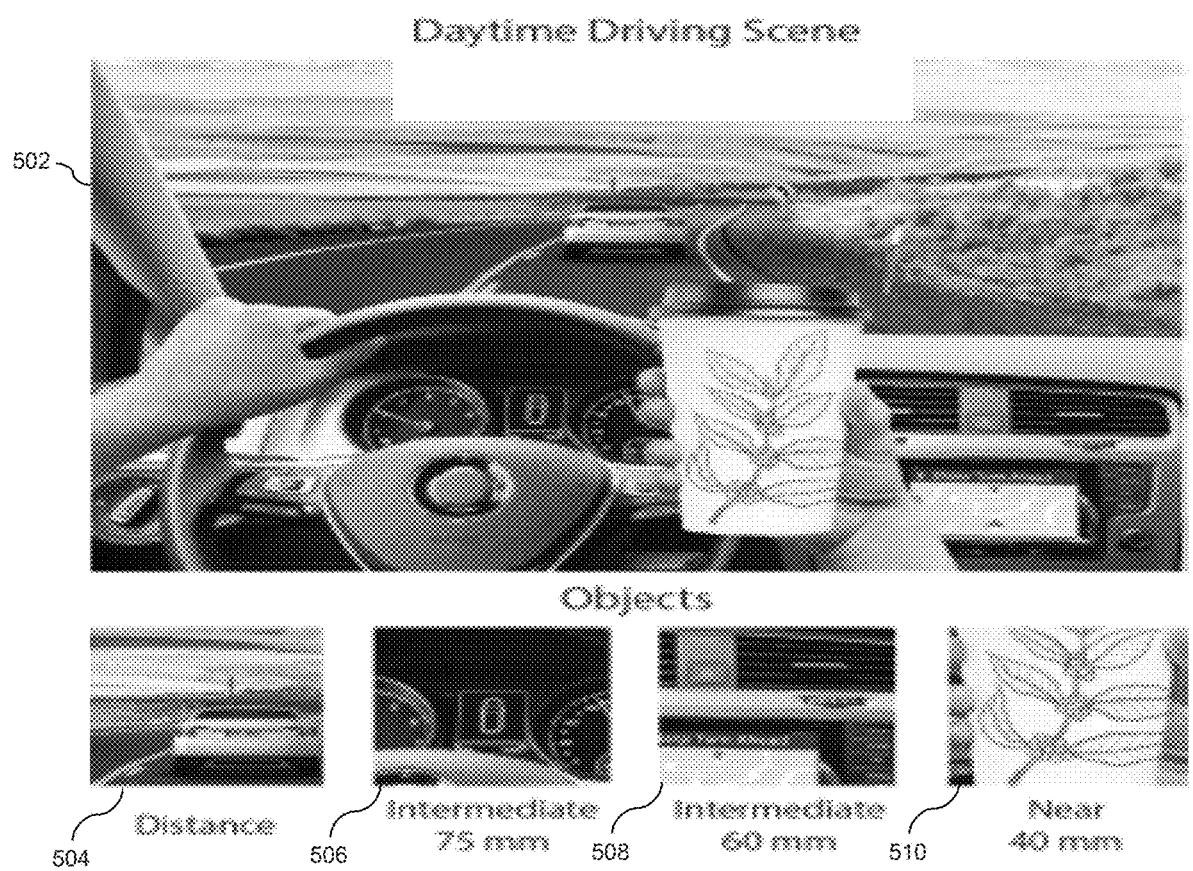
FIG. 5A illustrates another composite image representing a daytime scene according to some embodiments.

FIG. 5A illustrates another composite image 502 representing a daytime driving scene by combining different image layers 504-510. In this example, the image layer 504 represents objects (e.g., other cars, the road, other background objects) that are at a far viewing distance, the image layer 506 represents objects (e.g., the dashboard of the car) that is at an intermediate viewing distance (e.g., 75 cm), the image layer 508 represents objects (e.g., the computer screen of the car) that is at another intermediate viewing distance (e.g., 60 cm), and the image layer 510 represents objects (e.g., the coffee cup) that is at a near viewing distance (e.g., 40 cm).

Figure 4A:
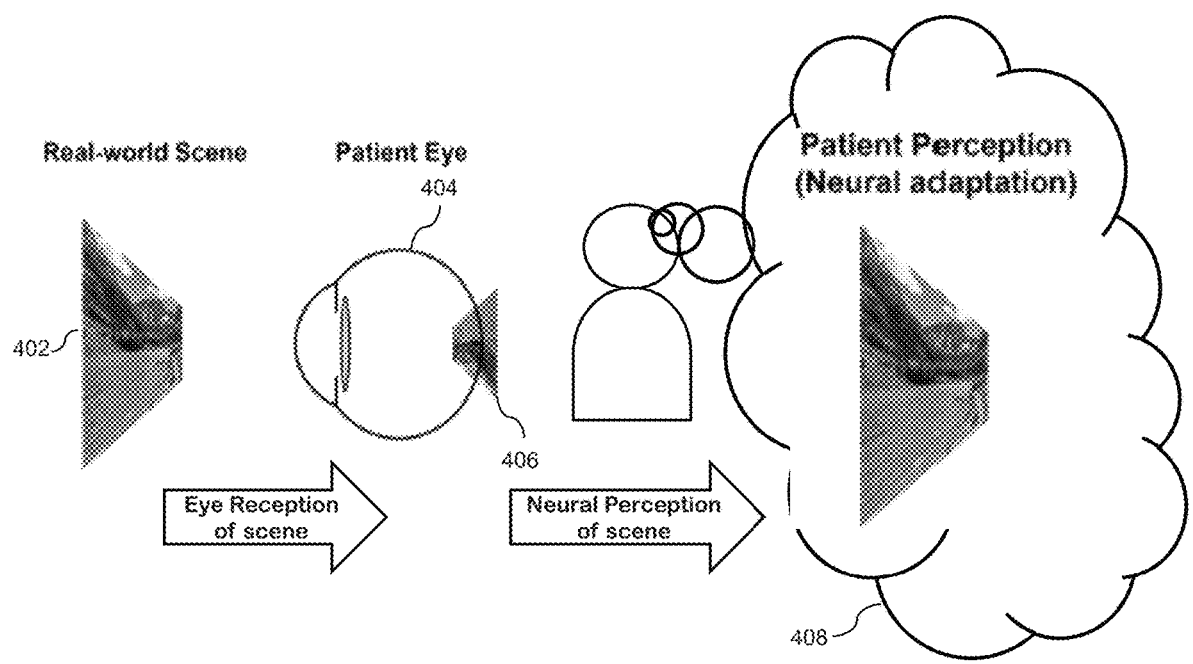
FIG. 4A illustrates a human perception of a real-world scene according to some embodiments.

FIG. 4A illustrates how a patient may perceive a real-world scene 402. The light from the real-world scene first passes through the eye optics 404 of the patient, where different portions of the real-world scene 402 (e.g., light reflected off of different portions of the real-world scene 402) may be blurred due to the eye optics 404, to form a retinal image 406. The retinal image 406 then reaches the brain of the patient, which may perform additional processing (e.g., increasing contrast, neural adaptation, etc.) to the retinal image 406 to generate the neural perception 408 of the real-world scene 402. Thus, to simulate how the retinal projection of objects in a real-world scene are blurred through the optics of the patient's eye, a first eye model that represents the optics of the patient's eye is obtained. As such, at step 210, the process 200 establishes a first eye model that represents a patient's eye.

Optical properties of a human eye can be described by a wavefront of the whole eye. The wavefront is characterized at the pupil (e.g., corneal) plane of the eye, which measures the total optical aberration of the human eye. To simulate the wavefront of a pseudophakic eye implanted with an IOL, a two-surface reduced eye model may be constructed. The two-surface reduced eye model includes two surfaces: one for the cornea of the patient's eye and one for the IOL. The corneal surface may have a higher-order aberration, and the surface for the IOL includes the optical diffractive structure by the design of the IOL. In some embodiments, the biometric information (e.g., a pupil diameter, an anterior chamber depth, a corneal power, etc.) represented by the eye model can be obtained by obtaining measurements of the patient's eye (e.g., using a diagnostic device). In some embodiments, the biometric information can be obtained based on clinical data gathered from pseudophakic eye that have previously undergone cataract surgery. For example, mean values of these biometrics from the clinical data can be used to represent an average pseudophakic eye. Corneal astigmatism, and the toric component of the IOL surface can be combined at the corneal plane in the eye model. Defocus (blurring) can be varied at the corneal plane based on different viewing distances, in order to calculate the vision of the pseudophakic patient for the different viewing distances. Table 1 below represents exemplary parameters of the two-surface reduced eye model.

TABLE 1

Key parameters of the two-surface reduced eye model.

| Description | Values |
| --- | --- |
| Refractive index of aqueous humor ($n_{aqueous}$) | 1.336 |
| Pupil diameter | Photopic: Mean 3.50 mm, SD +/− 0.8 mm<br>Mesopic: Mean 4.50 mm, SD +/− 0.8 mm |
| Anterior chamber depth, including central corneal thickness (ACD) | Mean 4.6 mm, SD +/− 0.3 mm |
| Corneal power ($K_{cornea}$) | Mean 43.4D, SD +/− 2.2D |
| Anterior corneal higher-order aberration | Zernike coefficients ($Z_3^{-3}$ to $Z_6^6$) |

In some embodiments, the optical performance of the human eyes can be quantified using various optical metrics either computed directly from the wavefront of the eye, or from a point-spread function (PSF). PSF represents the transformation associated with the wavefront at the image plane of the eye (e.g., the retina of the eye), which qualifies how light from objects at different viewing distances are focused (and/or blurred) by the eye of the patient based on the properties of the eye optics of the patient in forming retinal images. The PSF can be calculated using units of visual angle (radian) for the object space. A Fourier transformation of PSF may produce an optical transfer function (OTF), or the modulation transfer function (MFT) of the eye. While the PSF is in the spatial domain, the OTF expresses the PSF in the spatial frequency domain. The MFT, on the other hand, is the modulus of the OTF, which is related to the sensitivity of the human eye to contrast stimuli at different spatial frequencies. The PSF, the OTF, and the MFT all describe properties of the eye optics in forming a retinal image (e.g., the retinal image 406).

In some embodiments, the first eye model can be generated using the PSF based on the biometric information of the patient's eye (or the biometric information calculated using the clinical data). For example, the simulation manager 104 may generate the first eye model (e.g., the patient eye model 106) by calculating the PSF using the biometric information. The simulation manager 104 may then add defocus (e.g., blurring) and corneal astigmatisms at the corneal plane in the first eye model. The amount of defocus added to the first eye model may be proportional (or inversely proportional) to the viewing distance. Furthermore, the amount of corneal astigmatism added at the corneal plane in the first eye model may depend on whether the pseudophakic eye of the patient was implanted with non-toric or toric IOLs. In some embodiments, no anterior corneal higher-order aberration (HOA) is used to generate the first eye model. Diffractive optical design profile of the IOL can be expressed as the wavefront, and projected from the IOL plane to the corneal plane with scaling. The scaling factor $\gamma_{PatientEye}$ can be calculated using the following equation:

$$\gamma_{PatientEye} = \frac{n_{aqueous}/K_{cornea}}{n_{aqueous}/K_{cornea} - ACD} = 1.176 \qquad (3)$$

Entrance pupil size can be set according to the light condition of the intended real-world scenes. Stile-Crawford effect of the eye can be included in the calculation as pupil apodization. In some embodiments, monochromatic light having a wavelength of 550 nm can be used in the calculation of the PSF.

Once the first eye model (e.g., the patient eye model 160) is generated, the simulation manager 104 may store the first eye model 160 in the database 114. In some embodiments, to simulate how the retinal projection of objects in a real-world scene (e.g., the real-world scene 402) are blurred through the optics of the patient's eye, the simulation manager 104 may use the first eye model 160 (which represents the eye optics of the patient's eye), for example, the PSF calculated using the techniques described herein, to modify the composite image (e.g., the composite image 304) to form a simulated image. For example, the simulation manager 104 may convolve the first eye model (e.g., the PSF) with corresponding image layers (e.g., the image layers 306a-306c) in the composite image (e.g., the composite image 304), as illustrated in the equation below:

$$\text{Image}_{PatientEye}^{layer} = \text{PSF}_{PatientEye}^{layer} \otimes \text{Image}_{realWorldScene}^{layer} \qquad (4)$$

Where the symbol '⊗' stands for image convolution, and the super-script 'layer' denotes the calculation that is carried out for each layer in the composite image.

The simulation manager 104 may then generate the simulated image by merging the different modified image layers (e.g., each image layer being modified by convolving the first eye model 160 with the corresponding image layer) one by one according to the assumed viewing distance from far to near. In some embodiments, in order to ensure that the simulated image reflects the object occlusion and boundaries of the real-world scene 402, the simulation manager 104 may merge the different modified image layers using an alpha-blending method. For example, the simulation manager 104 may calculate the alpha values used for the blending by convolving the alpha channels for each image layer with the corresponding PSF, as illustrated in the following equation:

$$\text{Alpha}_{PatientEye}^{layer} = \text{PSF}_{PatientEye}^{layer} \otimes \text{Alpha}_{realWorldScene}^{layer} \quad (5)$$

In some embodiments, the simulation manager 104 may alpha-blend the different modified image layers using the following equation, according to the assumed viewing distances from far to near:

$$\text{Alpha}_{precedingLayer} = 1 - \text{Alpha}_{currentLayer} \quad (6)$$

Figure 4B:
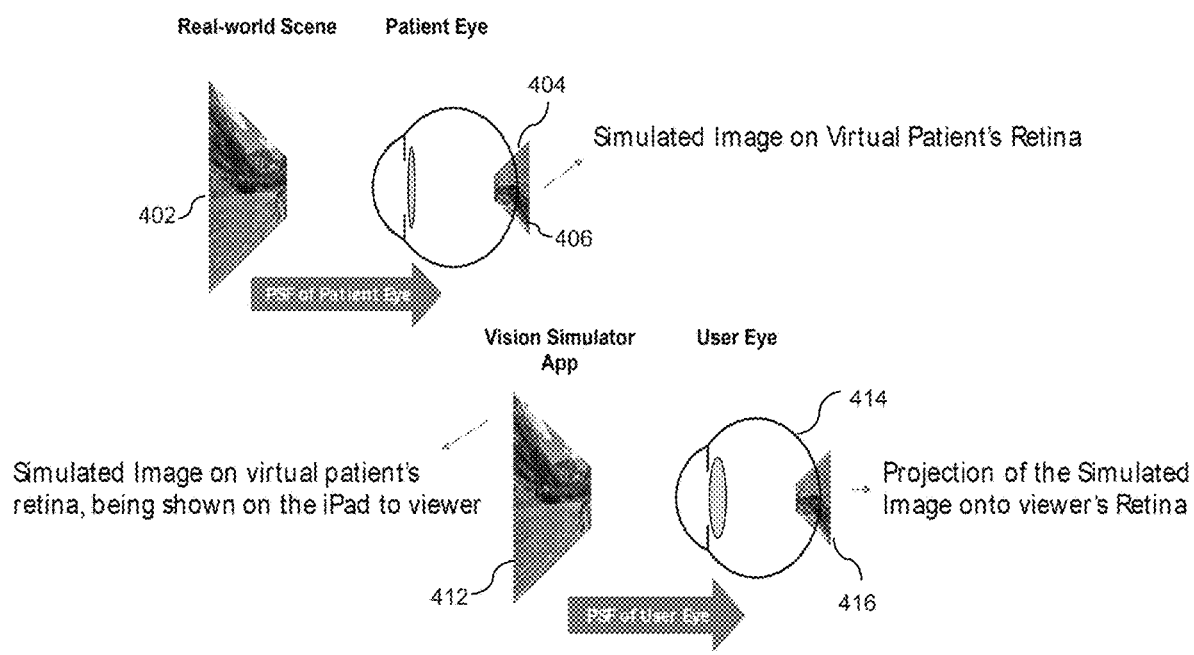
FIG. 4B illustrates a double pass effect according to some embodiments.

However, as discussed herein, the simulated image generated by convolving the first eye model 160 with the image layers using the technique described above may not capture the additional visual processing within a human visual system, such as potential neural adaptation for enhanced contrast perception with higher gain for a neural transfer function (NTF). Further, the simulated image also does not take into account the impact of the eye optics of a viewer when the simulated image is viewed by the viewer. As shown in FIG. 4B, the simulated image 412 is generated based on the first eye model 160, which simulates how the patient perceives the real-world scene 402 (e.g., the perceived image 406). However, when the user views the simulated image 412, the simulated image 412 will pass through the eye optics of the user's eye 414 and further processing by the user's brain before forming the user's perception 416 of the simulated image 412. Since the simulated image is viewed through the optics of the viewer's eye, there will be additional loss of image contrast, particularly at high spatial frequencies, which leads to less appreciation of the spatial clarity in the patient's vision using the IOL. This degradation of image quality is often referred to as a double-pass effect. Thus, the user's perception of the simulated image 416 is not the same as the simulated image 412.

The double-pass effect may arise in the viewer's eye (e.g., the user's eye), when the simulated image shown on the display is seen by the viewer. The double-pass effect referred herein describes the phenomenon that the simulated image, which was generated by applying the first eye model associated with the eye patient to a real-world scene, when viewed by the viewer, is further processed (e.g., blurred) by the eye optics of the viewer's eye before being registered by the viewer. Thus, how the viewer perceives the simulated image may be different from the simulated image. As such, the simulated image is perceived as being further processed (e.g., blurred) by the eye optics of the viewer (e.g., the user) when the image is registered by the viewer, as illustrated by the equation below:

$$\text{Image}_{viewerEye} = \text{PSF}_{viewerEye} \otimes \quad (7)$$
$$(\text{PSF}_{PatientEye} \otimes \text{Image}_{realWorldScene})$$
$$= (\text{PSF}_{viewerEye} \otimes \text{PSF}_{PatientEye}) \otimes$$
$$\text{Image}_{realWorldScene}$$
$$\neq \text{Image}_{PatientEye}$$

As shown in Equation (7), the image formed in the back of the viewer's eye is different from what was simulated for the patient's eye, due to the double-pass effect. Thus, in order for the viewer of the simulated image to perceive what the patient actually perceives when viewing the real-world scene (e.g., to eliminate the double-pass effect), the effect of the eye optics of the viewer needs to be subtracted from the simulated image before presenting the simulated image on the display (e.g., pre-compensating the optical blur of the viewer's eye in the simulated image).

First, the simulated image can be generated by the simulation manager 104 using the following equation, which does not take into account of the eye optics of the viewer's eye:

$$\text{Image}_{PatientEye} = \text{PSF}_{PatientEye} \otimes \text{Image}_{realWorldScene} \quad (8)$$
$$= \mathcal{F}^{-1}\{\mathcal{F}(\text{PSF}_{PatientEye} \otimes \text{Image}_{realWorldScene})\}$$
$$= \mathcal{F}^{-1}\{\mathcal{F}(\text{PSF}_{PatientEye}) \cdot \mathcal{F}(\text{Image}_{realWorldScene})\}$$
$$= \mathcal{F}^{-1}\{\text{OTF}_{PatientEye} \cdot \mathcal{F}(\text{Image}_{realWorldScene})\}$$

Where '$\mathcal{F}(\ )$' stands for Fourier transform and '$\mathcal{F}^{-1}$' stands for inverse Fourier transform. $\text{OTF}_{PatientEye}$ is the optical transfer function of the patient's eye, which is the Fourier transform of $\text{PSF}_{PatientEye}$.

To correct the double-pass effect, the simulation manager 104 of some embodiments may generate a second eye model (e.g., the user eye model 108) that represents the eye optics of the viewer. Thus, the process 200 obtains (at step 215) a second eye model representing a user's eye. In some embodiments, the simulation manager 104 may obtain biometric information of an eye of the user (e.g., the viewer) who will be viewing the simulated image (e.g., through a diagnostic device, etc.). Instead of measuring biometric information of each and every user, the simulation manager 104 of some embodiments may simply generate a generic eye model based on an eye of an "average" person (e.g., based on clinical data related to patients having healthy eyes (normal eye sight within a predetermined eye power range) obtained in the past). The simulation manager 104 may then generate the second eye model 108 based on the biometric information of the viewer using the techniques described herein by reference to generating the patient eye model 106. For example, the second eye model 108 may also be expressed as one or more PSFs, which can also be translated into OTFs and/or MTFs.

To take into account of the eye optics of the viewer, the simulated image can be generated by the simulation manager 104 using the following equation:

$$\text{Image}_{doublePassCorrection} = \mathcal{F}^{-1}\left\{\frac{\text{OTF}_{PatientEye}}{\text{OTF}_{viewerEye}} \cdot \mathcal{F}(\text{Image}_{realWorldScene})\right\} \quad (9)$$

In some embodiments, due to the variation of eye aberration between different viewers, the simulation manager 104 may replace $OTF_{PatientEye}$ with an average modulus transfer function (MTF) of human eyes ($MTF_{averageViewerEye}$), as illustrated in the following equation:

$$Image_{doublePassCorrection} = \qquad (10)$$
$$\mathcal{F}^{-1}\left\{\frac{OTF_{PatientEye}}{MTF_{averageViewerEye}} \cdot \mathcal{F}(Image_{realWorldScene})\right\}$$

It is noted that the $MTF_{averageViewerEye}$ can be replaced with $MTF_{viewerEye}$ if biometric information of the viewer is obtained. While using the MTF of an average viewer ignores individual variation in both phase and magnitude components of $OTF_{viewerEye}$, since $MTF_{averageViewerEye}$ describes how contrasts at different spatial frequencies are being transmitted through the optics of an average viewer's eye, it preserves the key optics characteristics relate to the simulation. The inverse of the second eye model (e.g., $1/MTF_{averageViewerEye}$) in Equation (10) compensates for the average contrast loss due to the double-pass effect of viewer's eye. Equation (10) can also be expressed as follows:

$$Image_{doublePassCorrection} = \mathcal{F}^{-1}\left\{\frac{OTF_{PatientEye}}{MTF_{averageViewerEye}} \cdot \mathcal{F}(Image_{realWorldScene})\right\} \qquad (11)$$
$$= \mathcal{F}^{-1}\left(\frac{OTF_{PatientEye}}{MTF_{averageViewerEye}}\right) \otimes Image_{realWorldScene}$$
$$= PSF_{doublePassCorrection} \otimes Image_{realWorldScene}$$

Where $PSF_{doublePassCorrection}$ can be expressed as:

$$PSF_{doublePassCorrection} = \mathcal{F}^{-1}\left(\frac{OTF_{PatientEye}}{MTF_{averageViewerEye}}\right) \qquad (12)$$
$$= \mathcal{F}^{-1}\left\{\frac{\mathcal{F}(PSF_{PatientEye})}{MTF_{averageViewerEye}}\right\}$$

Referring back to FIG. 2A, the process 200 then generates (at step 220) a simulated image by modifying the composite image based on the first eye model and the second eye model. For example, the simulation manager 104 may use the image modification module 110 to modify the composite image (e.g., the composite image 304) based on the first eye model 106 and the second eye model 108 to generate a simulated image. In some embodiments, the image modification module 110 may use the Equations (11) and (12) to generate the simulated image, for example, by convolving the first eye model 106 (e.g., $PSF_{PatientEye}$) and an inverse of the second eye model (e.g., $1/MTF_{averageViewerEye}$) with the each image layer in the composite image 304, and blending the modified image layers.

In addition to the eye optics of the viewer's eye, neural adaptation also plays a role in how the viewer perceives the simulated image. Neural adaptation is an ability of human vision system to adapt to visual blur. Specifically, when a retinal image (e.g., the retina image 406) is transmitted to a human brain, the brain may adapt the visual blurring caused by the eye optics (or other factors) by automatically increasing contrast sensitivity. In some embodiments, the simulation manager 104 may model the neural adaptation of an average human eye as an increase in gain of a neural transfer function. The simulation manager 104 then use the same techniques describe above by reference to the double-pass correction to apply the effect of the neural adaptation in the simulated image. For example, the simulation manager 104 may directly apply a neural adaptation model to (e.g., convolve with) the composite image (in addition to the first eye model and the second eye model) to generate the simulated image. In some embodiments, instead of generating another model, the simulation manager 104 may simply apply the contrast increase effect of the neural adaptation in the second eye model before applying the PSF of the double pass effect to the composite image.

The process 200 then presents (at step 225) the simulated image to a user via a display device and instructs (at step 230) the user to view the presented image at a particular distance associated with the first eye model. For example, the simulation manager 104 may transmit the simulated image to the display device 140 for display on the display device 140. It is noted that the double-pass correction is accurate only when the display device is placed at specific viewing distance to recreate the same viewing condition for the patient, such that the viewer may experience the spatial scale in the real-world scene (e.g., the real-world scene 402). As discussed above, the composite image (e.g., the composite image 304) was calibrated such that each pixel subtends a specific visual angle for a display device of a specific screen size and viewed at a specific viewing distance. Thus, the simulated image needs to be shown at a specific magnification (e.g., viewing distance from the viewer's eyes), so that the physical visual angles subtended by the image pixels on the display screen to the viewer's eyes are the same as the ones assumed for the patient's eye in the simulation. In other words, objects in the image subtends the same visual angel to the viewer as the objects in the real-world scene to the patient. For example, the simulation manager 104 may present the simulated image at the predetermined magnification and may instruct (e.g., via the display device 140) the viewer to view the simulated image at a viewing distance of 40 cm.

Figure 2B:
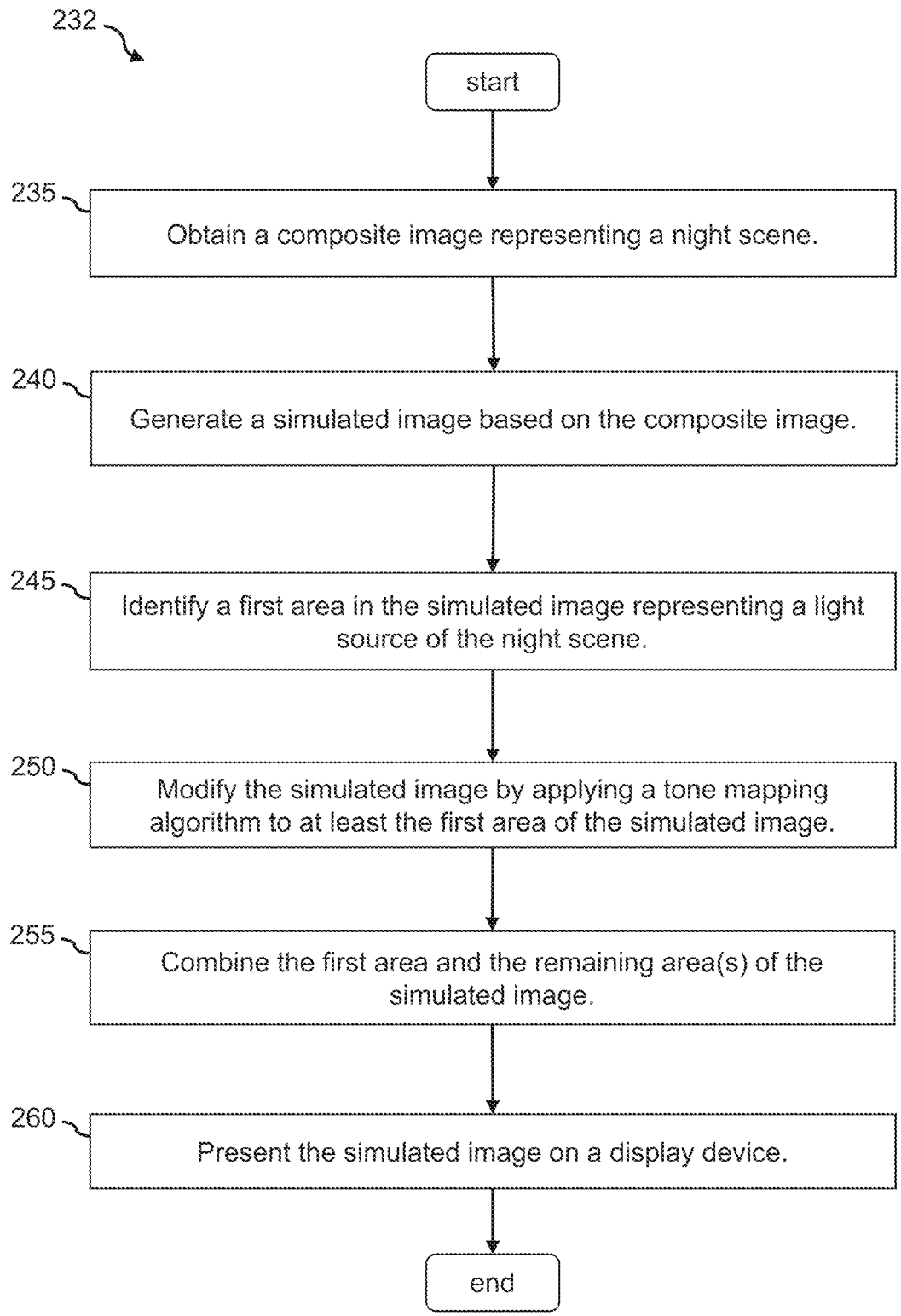
FIG. 2B illustrates a process of generating a simulated image representing a nighttime scene according to some embodiments.

The techniques described above is effective in simulating a patient's vision of a daytime scene. For a nighttime scene, the vision simulation system needs to take into account additional factors, such as the potential higher dynamic range of the nighttime scene, a human's perception of light intensity (e.g., lightness) in the dark, and the impact of light source intensity (e.g., potentially causing visual disturbance such as halo, starburst, etc.). As such, to simulate a patient's vision of a nighttime scene, the composite image obtained for the nighttime scene needs to have high dynamic range (HDR), so that the pixel intensity is linear to the physical intensities of the light sources. FIG. 2B illustrates a process 232 for generating a simulated image representing a patient's perception of a nighttime scene according to one embodiment of the disclosure. In some embodiments, the process 232 may be performed by the vision simulation engine 102. The process 232 begins by obtaining (at step 235) a composite image representing a nighttime scene.

Figure 5B:
FIG. 5B illustrates another composite image representing a nighttime scene according to some embodiments.

FIG. 5B illustrates a composite image 520 of a nighttime driving scene. Similar to the composite image 304 representing the daytime scene, the composite image 520 also includes multiple image layers, each image layer representing objects that is at a different viewing distance. For example, the composite image 520 may include an image layer that represents objects (e.g., the road, opposing car, etc.) that are at a far viewing distance, an image layer that represents objects (e.g., the dashboard and the screen in the car) that are at an intermediate viewing distance, and an image layer that represents objects (e.g., coffee cup) that are at a near viewing distance. The composite image 520 is a high dynamic range (HDR) image as the pixel values in the composite image 520 represents realistic physical light intensities in the nighttime scene. For example, the pixels representing light sources (e.g., car headlights, road lamps, etc.) in the composite image 520 have pixel values representing light intensities (e.g., luminance) in the order of 10,000 cd/m² or higher while the pixels representing non-light source have pixel values representing light intensities in the order of 1 cd/m².

The process 232 then generates (at step 240) a simulated image based on the composite image. For example, the simulation manager 104 may use the techniques described herein related to simulating a daytime scene (as described herein by reference to FIG. 2A) to process the HDR composite image (e.g., the composite image 520). For example, the simulation manager 104 may establish a first eye model that represents a patient's eye (the step 210 of FIG. 2A), obtain a second eye model that represents a viewer's eye (the step 215 of FIG. 2A), and generate a simulated image by modifying the composite image 520 based on the first eye model and the second eye model (e.g., using the Equations (12) and (13). Since the PSF(s) in the first eye model, which represents the eye optics of the patient's eye, take into account of how light (e.g., generated by light source of a scene) is spread when the light passes through the eye optics of the patient, by convolving the composite image with the first eye model, appropriate halos can be generated on the simulated image.

In some embodiments, the simulation manager 104 may use the nighttime simulation module 112 to further process the simulated image. For example, the simulation manager 104 may apply a tone mapping algorithm to the composite image 520 to compress the intensity range in the HDR image to a standard (or low) dynamic range such that the simulated image can be properly presented on a display device, which only has a standard (or low) dynamic range of display capability. In some embodiments, the simulation manager 104 may first segment the image into portions corresponding to light sources (e.g., a portion 522) and portions corresponding to non-light sources, and apply the tone mapping algorithm only to the light source portion 522 of the simulated image. The process 232 thus identifies (at step 240) a first area in the simulated image representing a light source of the night scene, modifies (at step 245) the simulated image by applying a tone mapping algorithm to at least the first area of the simulated image, and combines (at step 250) the first area and the remaining area(s) of the simulated image. In one specific example, the tone mapping algorithm defines a cutoff luminance value (e.g., 10,000 cd/m²), such that any pixels having luminance values above the cutoff luminance value (e.g., the pixels within the first area) is mapped to the maximum lightness value of the final simulated image (e.g., pixel value of 255), and pixels having luminance values below the cutoff luminance value is mapped to different lightness values according to a curve (e.g., in a linear manner, a non-linear manner, etc.). After applying the tone mapping algorithm to the simulated image, the process 232 presents (at step 260) the simulated image on a display device. For example, the simulation manager 104 may transmit the simulated image to the display device 140 for display on the display device 140.

In addition to simulating a vision of a patient who has her natural lens replaced by an IOL, the vision simulation engine 102 of some embodiments may also present a simulated image that simulates a vision of a patient who has other types of eye condition, such as a cataract eye condition, a presbyopic eye condition. To simulate a vision of a patient having cataract, the first eye model may be generated by the simulation manager 104 to represent the eye optics of an eye having a cataract condition. For example, the simulation manager 104 may model the wavefront of the cataract eye as a rough surface having spatial variation of phase delay. The roughness of the wavefront used in the simulation (both the magnitude of the spatial variation, and spatial frequency of the variation) increases with the severity of the cataract. The yellowing of the cataracts lens and the decreased light transmission through the lens were simulated by gradually decreasing the RGB pixel values of the simulated image.

Figure 6A:
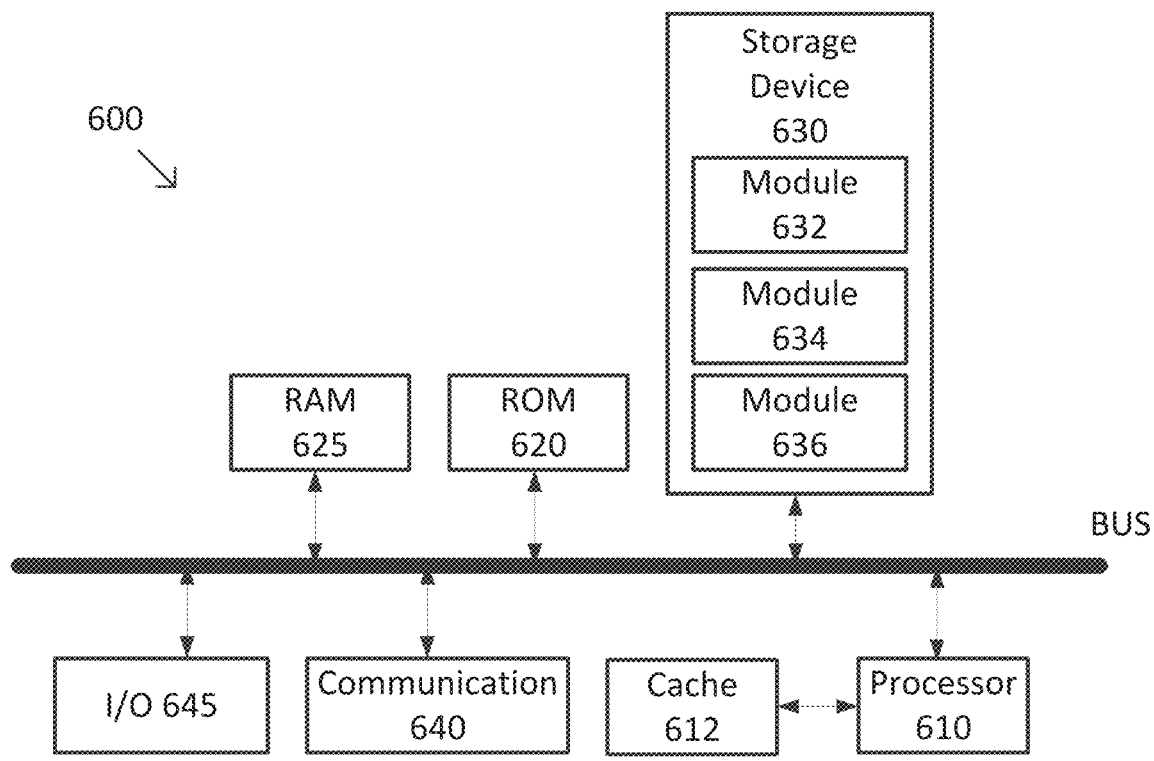
FIGS. 6A and 6B are diagrams of processing systems according to some embodiments.
Figure 6B:
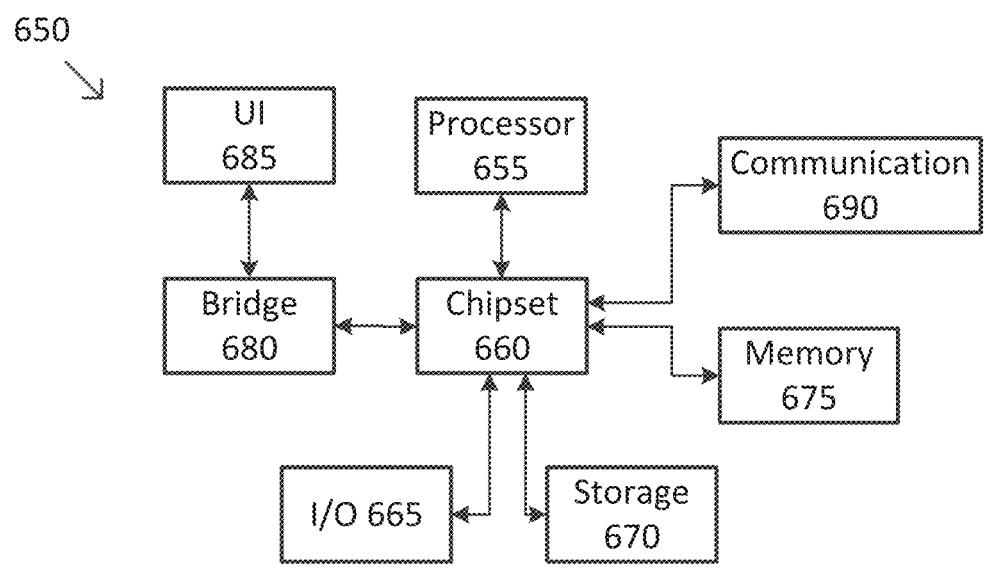

FIGS. 6A and 6B are diagrams of processing systems according to some embodiments. Although two embodiments are shown in FIGS. 6A and 46B, persons of ordinary skill in the art will also readily appreciate that other system embodiments are possible. According to some embodiments, the processing systems of FIGS. 6A and/or 6B are representative of computing systems that may be included in one or more of lens selection platform 102 and the ECP devices 130, 140, and 150, and/or the like.

FIG. 6A illustrates a computing system 600 where the components of system 600 are in electrical communication with each other using a bus 605. System 600 includes a processor 610 and a system bus 605 that couples various system components including memory in the form of a read only memory (ROM) 620, a random access memory (RAM) 625, and/or the like (e.g., PROM, EPROM, FLASH-EPROM, and/or any other memory chip or cartridge) to processor 610. System 600 may further include a cache 612 of high-speed memory connected directly with, in close proximity to, or integrated as part of processor 610. System 600 may access data stored in ROM 620, RAM 625, and/or one or more storage devices 630 through cache 612 for high-speed access by processor 610. In some examples, cache 612 may provide a performance boost that avoids delays by processor 610 in accessing data from memory 615, ROM 620, RAM 625, and/or the one or more storage devices 630 previously stored in cache 612. In some examples, the one or more storage devices 630 store one or more software modules (e.g., software modules 632, 634, 636, and/or the like). Software modules 462, 634, and/or 636 may control and/or be configured to control processor 610 to perform various actions, such as the processes of methods 300 and/or 500. And although system 600 is shown with only one processor 610, it is understood that processor 610 may be representative of one or more central processing units (CPUs), multi-core processors, microprocessors, microcontrollers, digital signal processors (DSPs), field programmable gate arrays (FPGAs), application specific integrated circuits (ASICs), graphics processing units (GPUs), tensor processing units (TPUs), and/or the like. In some examples, system 400 may be implemented as a stand-alone subsystem and/or as a board added to a computing device or as a virtual machine.

To enable user interaction with system 600, system 600 includes one or more communication interfaces 640 and/or one or more input/output (I/O) devices 645. In some examples, the one or more communication interfaces 640 may include one or more network interfaces, network interface cards, and/or the like to provide communication according to one or more network and/or communication bus standards. In some examples, the one or more communication interfaces 440 may include interfaces for communicating with system 600 via a network, such as network 115. In some examples, the one or more I/O devices 645 may include on or more user interface devices (e.g., keyboards, pointing/selection devices (e.g., mice, touch pads, scroll wheels, track balls, touch screens, and/or the like), audio devices (e.g., microphones and/or speakers), sensors, actuators, display devices, and/or the like).

Each of the one or more storage devices 630 may include non-transitory and non-volatile storage such as that provided by a hard disk, an optical medium, a solid-state drive, and/or the like. In some examples, each of the one or more storage devices 630 may be co-located with system 600 (e.g., a local storage device) and/or remote from system 600 (e.g., a cloud storage device).

FIG. 6B illustrates a computing system 650 based on a chipset architecture that may be used in performing any of the methods (e.g., methods 300 and/or 510) described herein. System 650 may include a processor 655, representative of any number of physically and/or logically distinct resources capable of executing software, firmware, and/or other computations, such as one or more CPUs, multi-core processors, microprocessors, microcontrollers, DSPs, FPGAs, ASICs, GPUs, TPUs, and/or the like. As shown, processor 655 is aided by one or more chipsets 660, which may also include one or more CPUs, multi-core processors, microprocessors, microcontrollers, DSPs, FPGAs, ASICs, GPUs, TPUs, co-processors, coder-decoders (CODECs), and/or the like. As shown, the one or more chipsets 660 interface processor 655 with one or more of one or more I/O devices 665, one or more storage devices 670, memory 675, a bridge 680, and/or one or more communication interfaces 690. In some examples, the one or more I/O devices 665, one or more storage devices 670, memory, and/or one or more communication interfaces 690 may correspond to the similarly named counterparts in FIG. 6A and system 600.

In some examples, bridge 680 may provide an additional interface for providing system 650 with access to one or more user interface (UI) components, such as one or more keyboards, pointing/selection devices (e.g., mice, touch pads, scroll wheels, track balls, touch screens, and/or the like), audio devices (e.g., microphones and/or speakers), display devices, and/or the like. According to some embodiments, systems 600 and/or 650 may provide a graphical user interface (GUI) suitable for aiding a user (e.g., a surgeon and/or other medical personnel) in the performance of the processes of methods 200 and 232.

Methods according to the above-described embodiments may be implemented as executable instructions that are stored on non-transitory, tangible, machine-readable media. The executable instructions, when run by one or more processors (e.g., processor 610 and/or processor 655) may cause the one or more processors to perform one or more of the processes of methods 200 and/or 210. Some common forms of machine-readable media that may include the processes of methods 200 and/or 210 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Devices implementing methods according to these disclosures may comprise hardware, firmware, and/or software, and may take any of a variety of form factors. Typical examples of such form factors include laptops, smart phones, small form factor personal computers, personal digital assistants, and/or the like. Portions of the functionality described herein also may be embodied in peripherals and/or add-in cards. Such functionality may also be implemented on a circuit board among different chips or different processes executing in a single device, by way of further example.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A system, comprising:
   a non-transitory memory; and
   one or more hardware processors coupled with the non-transitory memory and configured to read instructions from the non-transitory memory to cause the system to perform operations comprising:
   accessing a first eye model representing an eye of a patient and a second eye model representing an eye of a user different from the patient, wherein the first eye model represents a pseudophakic eye having a particular multi-focal intraocular lens, wherein the first eye model is associated with multiple magnifications and multiple viewing distances based on a visual angle;
   obtaining a composite image comprising a plurality of image layers corresponding to a scene, wherein each image layer in the plurality of image layers comprises an object associated with a real-world dimension and a real-world viewing distance in the scene;
   modifying the second eye model by performing a mathematical function to the second eye model;
   generating a simulated image by applying the first eye model and the modified second eye model to each image layer in the plurality of image layers of the composite image; and
   presenting the simulated image on a display device at a particular magnification from among the multiple magnifications and instructing a user to view the simulated image presented on the display device at a particular viewing distance from among the multiple viewing distances.

2. The system of claim 1, wherein the scene is a daytime scene, and wherein the modifying the second eye model comprises generating an inverse of the second eye model.

3. The system of claim 1, wherein the operations further comprise calibrating the composite image by determining, for the object in each image layer of the plurality of image layers, a viewing angle based on the associated real-world dimension and the real-world viewing distance.

4. The system of claim 1, wherein the operations further comprise generating the first eye model based at least in part on characteristics of the particular multi-focal intraocular lens.

5. A method, comprising:
   generating, by one or more hardware processors, a first eye model based on biometric information of an eye of a patient, wherein the first eye model represents a pseudophakic eye having a particular multi-focal intraocular lens, wherein the first eye model is associated with multiple magnifications and multiple viewing distances based on a visual angle;

accessing, by the one or more hardware processors, a second eye model representing an eye of a user different from the patient;

obtaining, by the one or more hardware processors, a composite image comprising a plurality of image layers corresponding to a scene, wherein each image layer in the plurality of image layers comprises an object associated with a real-world dimension and a real-world viewing distance in the scene;

modifying, by the one or more hardware processors, the first eye model based on the second eye model;

generating, by the one or more hardware processors, a simulated image by applying the first eye model to each image layer in the plurality of image layers of the composite image; and presenting the simulated image on a display device at a particular magnification from among the multiple magnifications and instructing a user to view the simulated image presented on the display device at a particular viewing distance from among the multiple viewing distances.

6. The method of claim 5, wherein the generating the simulated image further comprises blending the plurality of image layers.

7. The method of claim 5, wherein the scene is a nighttime scene, and wherein the method further comprises:

identifying a first area in the simulated image representing a light source of the scene; and modifying the simulated image by applying a tone mapping algorithm to pixels within the first area of the simulated image.

8. The method of claim 7, wherein the composite image is a high dynamic range image, wherein each pixel in the composite image represents real-world luminance intensity, and wherein the method further comprises converting the high dynamic range image to a standard dynamic range image associated with the display device.

9. The method of claim 5, wherein the first eye model comprises a point spread function.

10. The method of claim 5, wherein the generating the simulated image comprises convolving the first eye model with each image layer in the plurality of image layers.

11. A non-transitory machine-readable medium having stored thereon machine-readable instructions executable to cause a machine to perform operations comprising:

accessing a first eye model representing an eye of a patient and a second eye model representing an eye of a user different from the patient, wherein the first eye model represents a pseudophakic eye having a particular multi-focal intraocular lens, wherein the first eye model is associated with multiple magnifications and multiple viewing distances based on a visual angle;

obtaining a composite image comprising a plurality of image layers corresponding to a scene, wherein each image layer in the plurality of image layers comprises an object associated with a real-world dimension and a real-world viewing distance in the scene;

modifying the second eye model by performing a mathematical function to the second eye model;

generating a simulated image by applying the first eye model and the modified second eye model to each image layer in the plurality of image layers of the composite image; and presenting the simulated image on a display device at a particular magnification from among the multiple magnifications and instructing a user to view the simulated image presented on the display device at a particular viewing distance from among the multiple viewing distances.

12. The non-transitory machine-readable medium of claim 11, wherein the scene is a daytime scene, and wherein the modifying the second eye model comprises generating an inverse of the second eye model.

13. The non-transitory machine-readable medium of claim 11, wherein the scene is a nighttime scene, and wherein the operations further comprise:

identifying a first area in the simulated image representing a light source of the scene; and modifying the simulated image by applying a tone mapping algorithm to pixels within the first area of the simulated image.

\* \* \* \* \*